United States Patent [19]

Kulka et al.

[11] 4,287,100

[45] Sep. 1, 1981

[54] 1,2,3,6-TETRAHYDROBENZYL ALCOHOL ESTERS AND COMPOSITIONS CONTAINING THE SAME

[75] Inventors: Kurt Kulka, New York; Teodosij Zazula, Rego Park, both of N.Y.; John M. Yurecko, Jr., Bayonne, N.J.

[73] Assignee: Fritzsche Dodge & Olcott Inc., New York, N.Y.

[21] Appl. No.: 886,401

[22] Filed: Mar. 14, 1978

[51] Int. Cl.$^3$ .............................................. A61K 7/46
[52] U.S. Cl. .............................. 252/522 R; 560/106; 560/122; 560/220; 560/231
[58] Field of Search ................... 252/522; 260/586 R

[56] References Cited

U.S. PATENT DOCUMENTS 3,917,675  11/1975  Ochsner ............................. 252/522
3,963,675  6/1976  Naegli .............................. 260/586 R

FOREIGN PATENT DOCUMENTS 2826841  12/1978  Fed. Rep. of Germany.

OTHER PUBLICATIONS

Nordstrom, Chem. Ab. 74:32769h, 1971.
Kugatova et al., Chem. Ab. 55:22175h, 1961.
Petrov et al., Chem. Ab. 47:2735h, 1953.
Kugatova et al., Chem. Ab. 67:90430a, 1967.
Kogami et al., Chem. Ab. 76:34415y, 1972.
Petrov et al., Chem. Ab. 52:4516g, 1958.
Smit et al., Chem. Ab. 54:8887g, 1960; 57:12541e, 1962.
Schleppnik, Chem. Ab. 90:109808d, 1979.
S. Arctauder, Perfume and Flavor Chemicals, Published by Author, 1969, Montclair, N.J., Monographs 286; 294; 297; 301; 314; 332; 338; 346; 795; 797; 799.
Sopov et al., Chem. Ab. 59:7384e, 1963; 59:9827a, 1963; 61:5529, 1964; 62:14519g, 1965; 63:1712e, 1965; 63:6884h, 1965.

*Primary Examiner*—John F. Niebling
*Attorney, Agent, or Firm*—Cooper, Dunham, Clark, Griffin & Moran

[57] ABSTRACT

Esters of 1,2,3,6-tetrahydrobenzyl alcohol have been found to exhibit powerful odorous notes such as floral, woody and fruity notes, rendering such compounds valuable as fragrance materials either alone or in compositions. These 1,2,3,6-tetrahydrobenzyl alcohol esters are prepared by reacting 1,2,3,6-tetrahydrobenzyl alcohol with an appropriate organic acid.

11 Claims, No Drawings

1,2,3,6-TETRAHYDROBENZYL ALCOHOL ESTERS AND COMPOSITIONS CONTAINING THE SAME

BACKGROUND OF THE INVENTION 1,2,3,6-tetrahydrobenzyl alcohol, a known chemical, can be derived from 1,2,3,6-tetrahydrobenzaldehyde by reduction of the aldehyde group. 1,2,3,6-tetrahydrobenzoic acid, another known compound, derived from the same aldehyde has been reacted with alcohols to obtain aromatic esters useful as fragrances, see British Pat. No. 309,911.

It is well known in perfumery that esters of acids and esters of alcohols which have identical basic carbon skeletons have completely different sensory properties with regard to odor, e.g. benzyl acetate and ethyl benzoate, which respectively have the structures

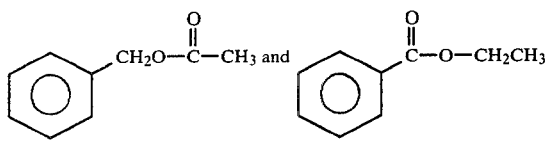

possess distinctive and different aromas.

It has now unexpectedly been found that esters of 1,2,3,6-tetrahydrobenzyl alcohol have great value as fragrance materials.

SUMMARY OF THE INVENTION

Specifically, this invention relates to novel esters of 1,2,3,6-tetrahydrobenzyl alcohol useful as fragrance materials and having the structure

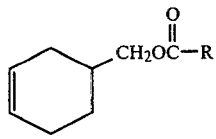

wherein R is hydrogen, an aliphatic group which is saturated or unsaturated, contains at most one double bond, and has 2 to 6 carbon atoms, a phenyl group, or a cyclopentyl group.

The invention further concerns fragrance compositions containing esters of 1,2,3,6-tetrahydrobenzyl alcohol having the structure

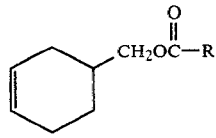

wherein R is hydrogen, an aliphatic group which is saturated or unsaturated, contains at most one double bond, and has 1 to 6 carbon atoms, a phenyl group, or a cyclopentyl group.

The esters of 1,2,3,6-tetrahydrobenzyl alcohol are prepared by reacting this alcohol with an organic acid having the structure RCOOH wherein R is hydrogen or a hydrocarbon group as indicated hereinabove. These esters are useful as fragrance materials.

Accordingly, one object of this invention is to provide compounds which are useful as fragrance materials.

Another object of this invention is to provide compositions containing the same and/or 1,2,3,6-tetrahydrobenzyl acetate which are useful as fragrance materials.

How these and other objects of this invention are accomplished will become apparent in light of the detailed description and claims which follow. In at least one embodiment of the practices of this invention at least one of the foregoing objects will be achieved.

DETAILED DESCRIPTION OF THE INVENTION

It has been discovered that compounds of the general structure

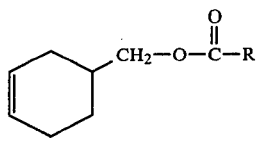

wherein R is hydrogen or an aliphatic group which is saturated or unsaturated, contains at most one double bond, and has 1 to 6 carbon atoms, a phenyl group, or a cyclopentyl group, exhibit odorous notes such as floral, woody and fruity notes making such compounds and compositions containing the same valuable and useful as fragrance adjuncts. Each of these compounds has a specific odor which is distinct and different from the next and each has its own specific and valuable odor-impact. Each compound has a pleasant and characteristic odor, and thus can be used directly or as part of a fragrant composition in amounts ranging from about 0.001 to 20% by weight thereof. Particularly desirable results are obtained with amounts in the range from 0.1 to 10%, but higher amounts of about 10 to 60% by weight are also useful.

The characteristic fragrances of a series of esters of 1,2,3,6-tetrahydrobenzyl alcohol including compounds wherein R is an alkyl, alkenyl having only one double bond, phenyl, or cyclopentyl are shown in Table I. Of these compounds all are new compounds except 1,2,3,6-tetrahydrobenzyl acetate. However, this compound has never before been known to be useful as a fragrance material and therefore, its use in fragrance compositions is one aspect of this invention.

TABLE I

| Compound | Characteristic Fragrance |
|---|---|
| 1,2,3,6-Tetrahydrobenzyl formate | Floral, spicy, cinnamon-clove character |
| 1,2,3,6-Tetrahydrobenzyl acetate | Floral, green, herbal, fresh hay |
| 1,2,3,6-Tetrahydrobenzyl propionate | Fruity, tutti-fruity |
| 1,2,3,6-Tetrahydrobenzyl isobutyrate | Floral, rose |
| 1,2,3,6-Tetrahydrobenzyl isovalerate | Top-note: cheesy, pleasant fruity main-character pineapple, tutti-fruity |
| 1,2,3,6-Tetrahydrobenzyl hexanoate | Fruity, sweet, pineapple |
| 1,2,3,6-Tetrahydrobenzyl benzoate | Nutty, floral, jasmine, honey-almond |
| 1,2,3,6-Tetrahydrobenzyl crotonate | Flowery, mushroom, rose, jasmine |
| 1,2,3,6-Tetrahydrobenzyl senecioate | Jasmine, floral |
| 1,2,3,6-Tetrahydrobenzyl cyclopentane carboxylate | Floral, fruity, peach |

The esters of 1,2,3,6-tetrahydrobenzyl alcohol are conveniently prepared by reacting this alcohol with an organic acid having the structure RCOOH wherein R is hydrogen, an aliphatic group which is saturated or unsaturated, contains at most one double bond, and has 1 to 6 carbon atoms, a phenyl group or a cyclopentyl group.

1,2,3,6-tetrahydrobenzyl alcohol is commercially available or is prepared from commercially available 1,2,3,6-tetrahydrobenzaldehyde. The method of preparing the alcohol from 1,2,3,6-tetrahydrobenzaldehyde is set forth more fully in Example 1. Examples 2–11 which follow describe the preparation of specific esters in accordance with this invention, but are not intended to limit in any way the scope thereof.

EXAMPLE 1

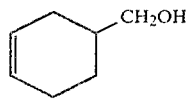

1,2,3,6-Tetrahydrobenzyl Alcohol
($C_7H_{12}O$ mol. wt. 112)

Reaction

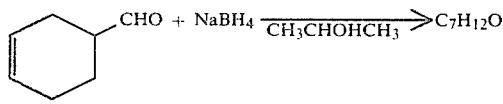

Procedure: (The Reaction was conducted in a Nitrogen Atmosphere)

The following were combined in a 12 liter flask fitted with an agitator, condenser, thermometer, nitrogen inlet, and an addition funnel.
2400 mls. incorporated
459 g. sodium borohydride (11.8% in sodium hydroxide solution, aqueous) agitated and cooled to 15° C.
Then the following was added over a one hour and 15 minutes period at 10°–20° C.—440 g. 1,2,3,6-tetrahydrobenzaldehyde.

Upon completion of addition the cooling bath was removed, and the reaction slurry was agitated for four hours and fifty minutes at a temperature between 16°–26° C.

Then with continued agitation, 500 mls. of water were added to dissolve the solids. The agitation was stopped, and the layers were separated. The lower aqueous layer was discarded.

The organic layer was cooled to 10°–15° C. in a 5 liter flask and acidified with 60 mls. of concentrated hydrochloric acid (acid to congo red).

The solution was agitated for 10 minutes, the excess acid was neutralized with a 10% aqueous sodium bicarbonate solution till slightly basic. Isopropanol was removed on a steam bath by distillation through a 6" packed column with an ejector vacuum. 200 mls. of hexane were added to the cooled residue. Washed with 5×75 mls. salt water. Reaction product: Neutral to Litmus. The solvent was removed by distillation on a steam bath through a 6" Vigreaux column with ejector vacuum—and the fractionation continued.

| Fraction | Temp. Vapor | Temp. Flask | mls. | wt. | R.I. 20° | Vac. | Remarks |
|---|---|---|---|---|---|---|---|
| I | 62°–94° C. | 97°–97½° C. | 2 | 2.1 g | 1.4780 | 20mm | Front |
| II | *94°–95° C. | 97½°–119° C. | 395 | 381.7 g | 1.4836 | 20mm | Main |
| III | *95°–95½° C. | 119°–129° C. | 8 | 6.8 g | 1.4836 | 20mm | Main |

Residue—37.2 g; Yield: theoretical: 448 g, actual: 388.5 g (86.7% of theory); Analysis: GLC—one peak—99.9% purity; $b_{20}$ 94°–95½° C.; $n_d^{20}$ 1.4836.

EXAMPLE 2

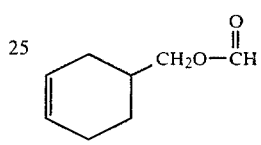

1,2,3,6-Tetrahydrobenzyl Formate
($C_8H_{12}O_2$ mol. wt. 140)

Reaction:

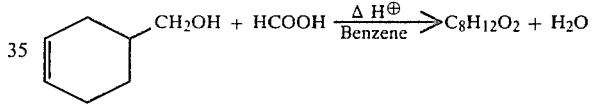

Procedure

The following were combined in a 500 ml. flask fitted with a thermometer and a Dean Stark water trap connected to a water cooled reflux condenser—
56 g. 1,2,3,6-tetrahydrobenzyl alcohol
25.3 g. formic acid (technical)
100 mls. benzene
0.1 g. p-toluenesulfonic acid
The above solution was heated to reflux.

Refluxing was continued for 52 minutes at a flask temperature between 87°–94° C. A total of 12 mls. of formic acid and water solution separated in the Dean Stark trap.

The aqueous layer was charged back into the reaction flask and refluxing continued for one hour till no more of the water was produced: A total of 12 mls. of aqueous material separated.

The reaction product was cooled and washed with:
2×100 mls. 10% aqueous sodium bicarbonate solution
4×75 mls. water until neutral to Litmus.
The solvent was removed on a steam bath by distillation with an ejector vacuum through a 6" Vigreaux column and fractionation continued.

| Fraction | Temp. Vapor | Temp. Flask | mls. | wt. | R.I. 20° | Vac. | Remarks |
|---|---|---|---|---|---|---|---|
| I | 71¼°–72° C. | 72¼° C. | 3 | 3.9g | 1.4630 | 10mm | |
| II | 72°–73° C. | 72½°–78° C. | 58 | 60.1g | 1.4636 | 10mm | Main |

Residue—3 g; Yield: theoretical: 70 g, actual: 60.1 g (85.9% of theory); Analysis: GLC—96.3290% purity; $b_{10}$ 72°–73° C.; $n_d^{20}$ 1.4636.

EXAMPLE 3

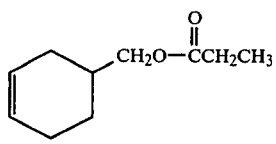

1,2,3,6-Tetrahydrobenzyl Propionate
($C_{10}H_{16}O_2$ mol. wt. 168)

Reaction:

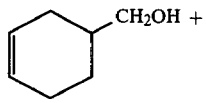

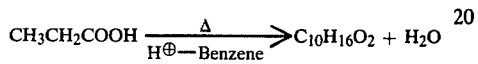

Procedure

The following were combined in a 500 ml. flask fitted with a thermometer, and a Dean Stark water trap connected to a water cooled condenser—
56 g. 1,2,3,6-tetrahydrobenzyl alcohol
40.7 g. propionic acid
100 ml. benzene
0.5 g. p-toluenesulfonic acid
The above solution was heated to reflux collecting the water of reaction in the trap.
  Time at reflux—5 hours and 14 minutes
  Temp. flask—84°–96½° C.
  Mls. collected: 9.8 (Theory 9 ml) $H_2O$
Reaction product cooled to room temperature and washed with:
2×50 mls. 10% aqueous sodium carbonate solution.
4×50 mls. water until neutral to Litmus.
The solvent was removed on a steam bath by distillation with ejector vacuum through a 6″ Vigreaux column and the fractionation continued.

EXAMPLE 4

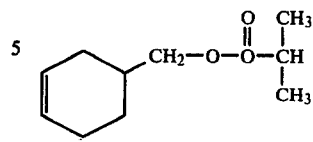

1,2,3,6-Tetrahydrobenzyl Isobutyrate
($C_{11}H_{18}O_2$ mol. wt. 182)

Reaction:

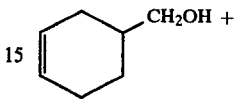

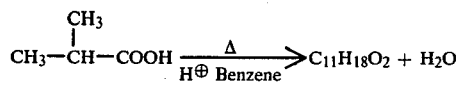

Procedure

The following were combined in a 500 ml. flask fitted with a thermometer aand a Dean Stark trap connected to a water cooled reflux condenser.
42.5 g. 1,2,3,6-tetrahydrobenzyl alcohol
41.5 g. isobutyric acid
0.5 g. p-toluenesulfonic acid
100 mls. benzene
The above solution was heated to reflux removing the water formed as an azeotrope of benzene and water.
  Time of heating at reflux—7 hours and 50 minutes
  Temperature of flask at reflux—92°–95° C.
  Collected—7.5 mls. (Theory; 6.8 mls.) $H_2O$
The reaction product was washed with:
2×50 ml. 10% aqueous sodium carbonate solution
5×75 ml. water until neutral to Litmus.
The combined aqua washings were extracted with 75 ml. benzene, the extract washed with water until neutral to Litmus and combined with the main organic part.
The solvent was removed on a steam bath by distillation with ejector vacuum through a 6″ Vigreaux column and the fractionation continued—

| Fraction | Temp. Vapor | Temp. Flask | mls. | wt. | RI 20° | Vac: | Remarks |
|---|---|---|---|---|---|---|---|
| I | 77°–88½° C. | 88°–90° C. | 4 | 4.4g | 1.4546 | 5mm | Front |
| II | *88½°–89° C. | 90°–95° | ~56 | 58.9g | 1.4549 | 5mm | Main |

| Fraction | Temp. Vapor | Temp. Flask | mls. | wt. | RI 20° | Vac | Remarks |
|---|---|---|---|---|---|---|---|
| I | 82°–82½° C. | 84°–86° C. | 3 | 3.0g | 1.4550 | 5mm | Front |
| II | 82½°–83° C. | 84° C. | 79 | 79.2g | 1.4530 | 5mm | Main |

Residue—1 g. Yield: theoretical 84 g; actual 79.2 g (94.3%); Analysis: GLC—99.26%; $b_5$ 92½°–93° C.; $n_d^{20}$—1.4530.

Residue: 2.6 g. Yield: theoretical 69.1 g; actual 58.9 g (85.2% of theory); Analysis: GLC—99.4% purity; $b_5$ 88½°–89° C.; $n_d^{20}$ 1.4549

EXAMPLE 5

[cyclohexenyl-CH2O-C(=O)-CH2-CH(CH3)-CH3 structure]

1,2,3,6-Tetrahydrobenzyl Isovalerate
($C_{12}H_{20}O_2$ mol. wt. 196)

Reaction:

[cyclohexene-CH2OH] +

$$CH_3-CH(CH_3)-CH_2COOH \xrightarrow[\text{Benzene}/\Delta]{H^{\oplus}} C_{12}H_{20}O_2 + H_2O$$

Procedure

The following were combined in a 500 ml. flask fitted with a thermometer and a Dean Stark water trap connected to a water cooled reflux condenser—
56 g 1,2,3,6-tetrahydrobenzyl alcohol
56.1 g. isovaleric acid
0.5 g. p-toluenesulfonic acid &
100 mls. benzene The above solution was heated at reflux, at a temperature between 90°–97° C. for five hours and thirty minutes, collecting 10 mls. of water—(Theory 9 mls)
IR shows no (OH)

The reaction product was cooled and washed with—
2×50 mls. 10% aqueous sodium carbonate solution
4×50 mls. water solution, until neutral to Litmus.
The solvent was removed on a steam bath by distillation through a 6" Vigreaux column with ejector vacuum—
—and fractionation was continued through a 6" Vigreaux column.

| Fraction | Temp. Vapor | Temp. Flask | mls. | wt. | RI | Vac. | Remarks |
|---|---|---|---|---|---|---|---|
| I | 88°–102° C. | 102°–104° C. | 6 | 5.8 g | 1.4540 | 5mm | Front |
| II | 102°–103° C. | 104°–109½° C. | 93 | 86.1 g. | 1.4561 | 5mm | Main |

Residue: 2.6 g. Yield: theoretical 93.0 g; actual 86.1 g (87.9% of theory); Analysis: GLC—99.69% purity; $b_5$ 102°–103° C.; $n_d^{20}$ 1.4561

EXAMPLE 6

[cyclohexene-CH2O-C(=O)-(CH2)4CH3 structure]

1,2,3,6-Tetrahydrobenzyl Hexanoate
($C_{13}H_{22}O_2$ mol. wt. 210)

Reaction:

[cyclohexene-CH2OH] +

$$CH_3(CH_2)_4-COOH \xrightarrow[\text{Benzene}\ \Delta]{H^{\oplus}} C_{13}H_{22}O_2 + H_2O$$

Procedure

The following were combined in a 500 ml. flask fitted with a Dean Stark water trap connected to a water cooled reflux condenser and a thermometer—
56 g. 1,2,3,6-tetrahydrobenzyl alcohol
63.8 g. hexanoic acid
1 g. p-toluenesulfonic acid
100 ml. benzene The above solution was heated to reflux collecting the water formed in the trap.
Time of reflux: 4 hours and 5 minutes
Temperature in flask at reflux: 80°–97° C.
Collected: 9.2 mls. water (Theory—9 ml.) IR: No-OH present The reaction mixture was cooled to room temperature and washed with—
2×50 mls 10% sodium carbonate aqueous solution
3×75 mls. water until neutral to Litmus.
The solvent was removed on a steam bath by distillation with ejector vacuum through a 6" Vigreaux column—and the fractionation continued under a vacuum—of 2 mm.

| Fraction | Temp. Vapor | Temp. Flask | mls. | wt. | RI 20° | Vac: | Remark |
|---|---|---|---|---|---|---|---|
| I | 102°–106½° C. | 110°–111° C. | 2 | 13 g. | 1.4580 | 2mm | Front |
| II | 106½°–107° C. | 111°–114° C. | 90 | 88.6 g. | 1.4590 | 2mm | Main |

Residue—4 g. Yield: theoretical: 105 g; actual 88 g;
Analysis: GLC—99.464% purity; $b_2$ 106½°–107° C.; $n_d^{20}$ 1.4590

EXAMPLE 7

[cyclohexene-CH2O-C(=O)-phenyl structure]

1,2,3,6-Tetrahydrobenzyl Benzoate
($C_{14}H_{16}O_2$ mol. wt. 216)

Reaction:

[cyclohexene-CH2OH] +

[phenyl-COOH] $\xrightarrow[\text{Benzene}/\Delta]{H^{\oplus}} C_{14}H_{16}O_2 + H_2O$

Procedure

The following were combined in a 500 ml. flask fitted with a thermometer and a Dean Stark water trap connected to a water cooled reflux-condenser.

42.5 g. tetrahydrobenzyl alcohol
51.0 g. benzoic acid
0.5 g. p-toluenesulfonic acid
100 mls. benzene Heated to reflux for 2 hours and 30 minutes at a flask temperature between 89°–92° C. collecting: 3 mls. of water.

The reaction product was cooled and stood overnight at room temperature.

The next day an additional 0.5 g. of p-toluenesulfonic acid was added and continued heating at reflux (Flask Temperature 91°–93° C.) for 5½ hours—collecting a total of 6.3 mls. of water. (Theory—(6.8 mls.)).

The reaction product was cooled and washed with, 100 mls. 10% sodium carbonate aqueous solution 4×75 mls. water (salt solution) until neutral to Litmus. The solvent was removed by distillation from a steam bath and the reaction product fractionated through a 6″ Vigreaux column.

28 g. of 1,2,3,6-tetrahydrobenzyl alcohol
25.8 g. crotonic acid
100 ml. of benzene
0.5 g. of p-toluenesulfonic acid The reaction mixture was refluxed until no more water was formed.

Note: During the course of the reaction additional 0.5 g. of p-toluenesulfonic acid were added.

Time of reaction: 31½ hours.
Temperature of reaction: 91°–92°
Amount of water collected: 5.5 ml.

The reaction mixture was cooled to room temperature, neutralized with 10% aqueous sodium carbonate solution. Washed three times with 25 ml. of water until neutral to Litmus. The solvent was distilled off on steam bath, ejector vacuum. The reaction product was fractionated through a 6″ Vigreaux column.

| Fractionation through a 6″ Vigreaux Column | | | | | | | |
|---|---|---|---|---|---|---|---|
| Fraction | Temp. Vapor | Temp. Flask | Vac. | mls. | Wt. | R.I. 20° | Remarks |
| I | 77.5° | 82°–83° | 2mm | 2 ml. | 2 g. | 1.4802 | Front |
| II | 77.5–78.5° | 83°–95° | 2mm | 39 ml. | 39 g. | 1.4820 | Main |

Residue: 5 g. Yield: theoretical 45 g, actual 39 g (86.7% of theoretical); Analysis: GLC—99.9% purity; $b_2$ 77.5°–78.5° C.; $n_d^{20}$ 1.4820.

EXAMPLE 9

| Fraction | Temp. Vapor | Temp. Flask | mls. | wt. | RI 20° | Vac. | Remarks |
|---|---|---|---|---|---|---|---|
| I | 62°–138° C. | 110°–140° C. | 6 | 6.1g | 1.4978 | 2mm | |
| II | 138°–139½° C. | 140°–156° C. | 60 | 63.5g | 1.5331 | 2mm | Main |

Residue—4.5 g. Yield: theoretical: 82.1 g; actual 63.5 g (77.3% of theory) Analysis: GLC 99.86% purity; $b_2$ 138°–139° C.; $n_d^{20}$ 1.5331

EXAMPLE 8

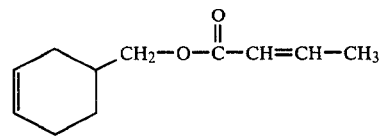

1,2,3,6-Tetrahydrobenzyl Crotonate
($C_{11}H_{16}O_2$ mol. wt. 180)

Reaction:

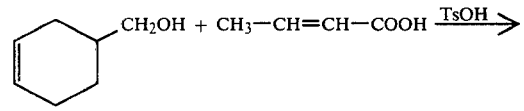

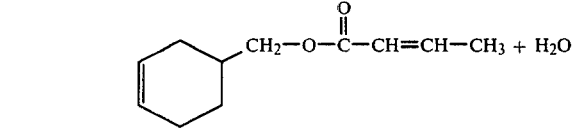

Procedure

The following were charged to a 500 ml. 3-neck flask fitted with an agitator, thermometer, reflux condenser and a water trap:

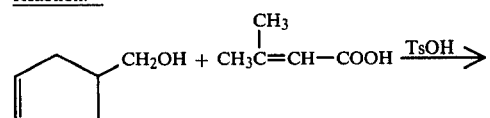

1,2,3,6-Tetrahydrobenzyl Senecioate
($C_{12}H_{18}O_2$ mol. wt. 194)

Reaction:

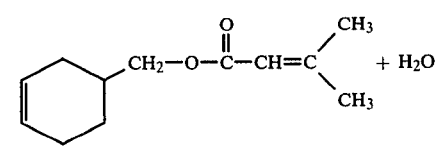

Procedure

The following were charged to a 500 ml. 3-neck flask fitted with an agitator, thermometer, reflux condenser and a watet trap:

28 g. 1,2,3,6-tetrahydrobenzyl alcohol
30 g. senecioic acid
1.5 g. p-toluenesulfonic acid
100 ml. benzene The reaction mixture was refluxed with water trap.
Time of reaction: 27 hours and 45 minutes Temperature of reaction: 87°–89° C.
Amount of water collected: 4.5 ml. The reaction product was neutralized with a 10% aqueous sodium carbonate solution, washed two times with 30 ml. of water until neutral to Litmus.

The solvent was distilled off on steam bath—ejector vacuum.

The reaction product was fractionated through a 6" Vigreaux column.

| Fractionation through a 6" Vigreaux column | | | | | | | |
|---|---|---|---|---|---|---|---|
| Fraction | Temp. Vapor | Temp. Flask | Vac. | Vol. | Wt. | R.I. 20° | Remark |
| I | 80°–88° | 92°–104° | 2mm | 6 ml. | 6 g. | 1.4888 | Front |
| II | 88°–88.5° | 104°–121° | 2mm | 36 ml. | 35 g. | 1.4872 | Main |

Residue: 4 g. Yield: theoretical 48.5 g, actual 35 g (72.16% of theoretical) Analysis: GLC 99% purity, $b_2$ 88°–88.5° C., $n_d^{20}$ 1.4872

EXAMPLE 10

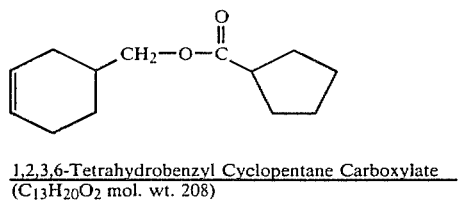

1,2,3,6-Tetrahydrobenzyl Cyclopentane Carboxylate
($C_{13}H_{20}O_2$ mol. wt. 208)

Reaction:

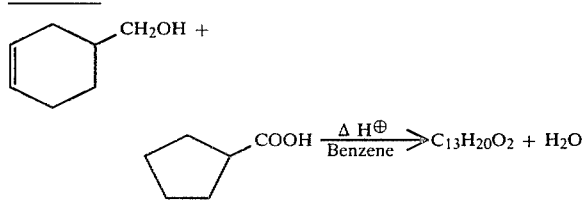

Procedure

The following were combined in a 300 ml. flask fitted with a thermometer and a Dean Stark trap connected to a water cooled condenser:
11.5 g. 1,2,3,6-tetrahydrobenzyl alcohol
12 g. cyclopentanecarboxylic acid
75 mls. benzene
0.2 g. p-toluenesulfonic acid The above solution was heated to reflux removing the water formed as an azeotrope of benzene and water.
Time of heating—16 hours at 45 minutes
Temperature in Flask at reflux—84°–88° C.
Collected: 1.6 mls. water The reaction product was cooled and washed with:
100 mls. of 10% sodium carbonate solution, aqueous
5×75 mls. water until neutral of Litmus.

The solvent was removed on a steam bath by distillation with ejector vacuum through a 6" Vigreaux column and the fractionation continued

| Fraction | Temp. Vapor | Temp. Flask | mls. | wt. | Vac. | R.I. | Remarks |
|---|---|---|---|---|---|---|---|
| I | 97°–97½° C. | 103°–105° C. | 3 | 2.8g | 0.5mm | 1.4810 | Front |
| II | 97½°–98° C. | 103°–105° | 18 | 15.6g | 0.5mm | 1.4814 | Main |

Residue—2.6 g. Yield: theoretical 21.4 g, actual 15.6 g (72.9% of theory) Analysis: GLC one peak (99.9%) purity $b_{0.5}$ 97½–98° C. $n_d^{20}$ 1.4814

EXAMPLE 11

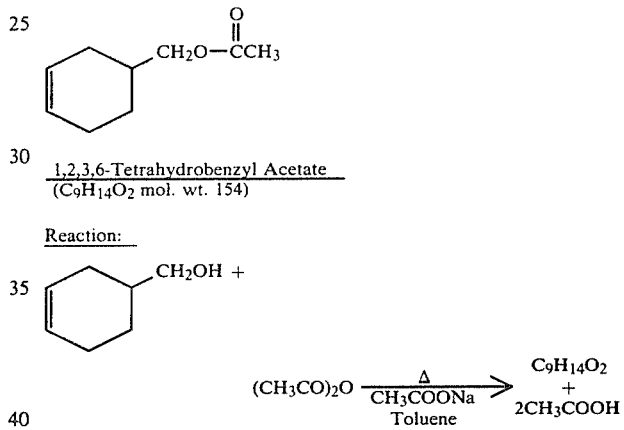

1,2,3,6-Tetrahydrobenzyl Acetate
($C_9H_{14}O_2$ mol. wt. 154)

Reaction:

Procedure

The following were combined in a 500 ml. flask fitted with a thermometer, 7" Vigreaux column, distilling condenser, and a receiver.
42.5 g. 1,2,3,6-tetrahydrobenzyl alcohol
60.5 g. acetic anhydride
300 mls. toluene
0.5 g. sodium acetate The reaction mixture was heated at a flask temperature of 114°–121° C. over a three hour and 50 minute period; distilling the azeotrope of acetic acid and toluene, at a vapor temperature of 104°–109° C. 178 mls. distillate were collected.

The excess acetic anhydride and toluene were removed from the reaction product by distillation from a steam bath under ejector vacuum through a 7" Vigreaux column. Then the last traces of low boilers were removed with a vacuum of 10 mm at a flask temperature of 80° C. The residue was cooled, and diluted with 150 mls. of hexane and washed with:
2×200 mls. 10% sodium carbonate aqueous solution
4×75 mls. water. The reaction product was neutral to Litmus.

The solvent was removed by distillation on a steam bath with ejector vacuum through a 6" Vigreaux column and fractionation continued.

| Fraction | Temp. Vapor | Temp. Flask | mls. | wt. | R.I. 20° | Vac. | Remarks |
|---|---|---|---|---|---|---|---|
| I | 85° C. | 86° C. | 4 | 4.0g | 1.4593 | 10mm | Front |
| II | 85°–86° C. | 86°–87° C. | 50 | 50.8g | 1.4594 | 10mm | Main |

Residue—3 g. Yield: theoretical 58.5 g., actual 50.8 g. (86.8% of theory); Analysis: GLC—99.74% purity; $b_{10}$ 85°–86° C.; $n_d^{20}$ 1.4594

The 1,2,3,6-tetrahydrobenzyl alcohol esters of this invention, as disclosed hereinabove are useful as fragrance materials or as components of perfume compositions containing other aroma chemicals. Accordingly, one or a combination of these compounds are useful as perfumes or as part of fragrance compositions or are generally usefully incorporated in other compositions, e.g. cosmetics, such as lotions and creams, soaps, room-sprays, and sachets in order to impart a desirable fragrance thereto.

When employed as perfumes, or in fragrant compositions or when employed in other compositions to impart a desired fragrance thereto, the compounds of this invention are incorporated therein in a amount effective to impart a desired fragrance, such as an amount in the range 0.001 to 20% by weight, usually an amount in the range 0.1 to 10% by weight.

Formulations of fragrances employing a compound in accordance with this invention are set forth hereinafter. Accompanying Table II shows the makeup of a Tutti Fruity fragrance employing the compounds 1,2,3,6-tetrahydrobenzyl isovalerate and 1,2,3,6-tetrahydrobenzyl proprionate; Table III shows a floral fragrance composition employing 1,2,3,6-tetrahydrobenzyl hexanoate and 1,2,3,6-tetrahydrobenzyl benzoate; Table IV, a new-mown hay fragrance composition employing 1,2,3,6-tetrahydrobenzyl acetate and 1,2,3,6-tetrahydrobenzyl isobutyrate; Table V, a chypre fragrance composition employing 1,2,3,6-tetrahydrobenzyl hexanoate; Table VI, a carnation fragrance composition containing 1,2,3,6-tetrahydrobenzyl formate; Table VII, a rose fragrance composition employing 1,2,3,6-tetrahydrobenzyl isobutyrate and 1,2,3,6-tetrahydrobenzyl crotonate; Table VIII, a floral composition (Phantasy Bouquet) employing 1,2,3,6-tetrahydrobenzyl senecioate and Table IX, a lilac fragrance composition employing 1,2,3,6-tetrahydrobenzyl cyclopentanecarboxylate.

TABLE II

Tutti Fruity

| % Wt. | Component |
|---|---|
| 0.52 | Ethyl Formate |
| 8.7 | Ethyl Caproate |
| 2.2 | Ethyl Propionate |
| 2.3 | Propyl Acetate |
| 0.72 | Isobutyl Acetate |
| 9.0 | Ethyl Butyrate |
| 5.9 | 1,2,3,6-Tetrahydrobenzyl Isovalerate |
| 0.81 | Ethyl Isovalerate |
| 10.9 | Isoamyl Acetate |
| 9.0 | 1,2,3,6-Tetrahydrobenzyl Propionate |
| 11.49 | Limonene |
| 0.6 | n-Butyl Butyrate |
| 0.25 | Ethyl Caproate |
| 0.81 | Isoamyl Butyrate |
| 2.3 | Ethyl Lactate |
| 0.7 | Ethyl Pelargonate |
| 14.45 | Carvone |
| 0.9 | Cinnamic Aldehyde |
| 18.0 | Eugenol |
| 0.45 | Heliotropin |

TABLE II-continued

Tutti Fruity

| % Wt. | Component |
|---|---|
| 100.0% | |

TABLE III

Floral

| % Wt. | Component |
|---|---|
| 17.1 | Amyl Salicylate |
| 17.1 | Isobutyl Salicylate |
| 8.6 | Linalool |
| 4.3 | Hydroxycitronellal |
| 4.9 | 1,2,3,6-Tetrahydrobenzyl Hexanoate |
| 5.7 | Heliotropin |
| 5.7 | 1,2,3,6-Tetrahydrobenzyl Benzoate |
| 3.4 | Coumarin |
| 1.4 | 2,4-Dihydroxy-3-methyl Benzoate |
| 8.6 | Phenylethyl Alcohol |
| 1.7 | Vanillin |
| 11.4 | Linalyl Acetate |
| 2.9 | Geranyl Acetate |
| 7.2 | Cassie Absolute |
| 100.0% | |

TABLE IV

New-Mown Hay

| % Wt. | Component |
|---|---|
| 12.5 | Oil Bergamot |
| 18.8 | Linalyl Acetate |
| 3.8 | Coumarin |
| 3.8 | Tonka Absolute |
| 3.8 | 1,2,3,6-Tetrahydrobenzyl Acetate |
| 2.5 | Dimethyl Hydroquinone |
| 1.2 | Oil Patchouly |
| 2.5 | 2,4-Dihydroxy-3-methyl Benzaldehyde |
| 1.2 | 1,2,3,6-Tetrahydrobenzyl Isobutyrate |
| 6.2 | Linalool |
| 12.5 | Linalyl Acetate |
| 1.2 | Oil Clary Sage |
| 28.1 | Hydroxycitronellal |
| 1.2 | Hexyloxyacetonitrile |
| 0.7 | 1,1,4,4-Tetramethyl-6-Ethyl-1,2,3,4-Tetrahydronaphthalene-7-Nitrile (Musk Nitrile) |
| 100.0% | |

TABLE V

Chypre

| % Wt. | Component |
|---|---|
| 13.3 | Linalool |
| 1.0 | Oil Lavender |
| 10.0 | Heliotropin |
| 16.7 | Oil Ylang Ylang |
| 6.7 | 1,2,3,6-Tetrahydrobenzyl Hexanoate |
| 16.6 | Oil Orange |
| 6.7 | Oil Geranium Bourbon |
| 3.3 | Hexyloxyacetaldehyde Dimethyl Acetal |
| | Hexyloxyacetaldehyde Dipropyleneglycol |
| 3.3 | Hemiacetal |
| 1.7 | Civet absolute |
| 4.0 | Labdanum Resinoid |
| 10.0 | Musk Xylol |
| 6.7 | 1,1,4,4-Tetramethyl-6-Ethyl-1,2,3,4-Tetrahydronaphthalene-7-Nitrile (Musk Nitrile) |
| 100.0% | |

TABLE VI

Carnation

| % Wt. | Component |
|---|---|
| 10 | Oil Pimento |
| 20 | Eugenol |
| 5 | Iso-Eugenol |
| 5 | 1,2,3,6-Tetrahydrobenzyl Formate |
| 5 | Oil Nutmeg |
| 5 | Oil Cananga |
| 3 | Methyl Ionone |
| 2 | Anisic Aldehyde |
| 10 | Geraniol |
| 10 | Oil Petitgrain Terpenless |
| 5 | Hexyloxyacetaldehyde Dimethyl-Acetal |
| 7 | 1,1,4,4-Tetramethyl-6-Ethyl-1,2,3,4-Tetrahydronaphthalene-7-Nitrile (Musk Nitrile) |
| 2 | Hexyloxyacetonitrile |
| 6 | Isobutyl Phenylacetate |
| 5 | Hydrocinnamic Aldehyde |
| 100% | |

TABLE VII

Rose

| % Wt. | Component |
|---|---|
| 48.9 | Phenylethyl Alcohol |
| 12.2 | Oil Geranium Palmarosa |
| 12.2 | Citronellol |
| 6.1 | Geraniol |
| 6.1 | Phenylethyl Butyrate |
| 6.1 | Phenylethyl Acetate |
| 0.6 | Rose Oxide |
| 0.6 | Nonyl Aldehyde |
| 1.2 | Methyl Ionone |
| 1.2 | 1,2,3,6-Tetrahydrobenzyl Isobutyrate |
| 0.6 | 1,2,3,6-Tetrahydrobenzyl Crotonate |
| 1.8 | Rhodinol Acetate |
| 0.5 | Musk Ketone |
| 0.7 | 1,1,4,4-Tetramethyl-6-Ethyl-1,2,3,4-Tetrahydronaphthalene-7-Nitrile (Musk Nitrile) |
| 1.2 | Alpha Terpineol |
| 100.0% | |

TABLE VIII

Phantasy Bouquet

| % Wt. | Component |
|---|---|
| 10 | Oil Neroli, bigarade |
| 10 | Oil Orange Blossom |
| 10 | 1,2,3,6-Tetrahydrobenzyl Senecioate |
| 8 | Coumarin |
| 4 | Vanillin |
| 4 | Hexyloxyacetaldehyde Dipropyleneglycol Hemi-Acetal |
| 8 | Alpha Ionone |
| 10 | Oil Vetiver |
| 20 | Phenylethyl Alcohol |
| 4 | Oil Clove |
| 4 | Oil Sandalwood |
| 4 | 1,1,4,4-Tetramethyl-6-Ethyl-1,2,3,4-Tetrahydronaphthalene-7-Nitrile (Musk Nitrile) |
| 2 | Musk Ketone |

TABLE VIII-continued

Phantasy Bouquet

| % Wt. | Component |
|---|---|
| 2 | Hexyloxyacetaldehyde Dimethyl Acetal |
| 100% | |

TABLE IX

Lilac

| % Wt. | Component |
|---|---|
| 60 | Alpha-Terpineol |
| 2 | Heliotropin |
| 10 | Oil Ylang-Ylang |
| 12 | Phenylethyl Alcohol |
| 5 | Methyl-Ionone |
| 1 | 1,2,3,6-Tetrahydrobenzyl cyclopentanecarboxylate |
| 10 | Resinoid Benzoin |
| 100% | |

As will be apparent to those skilled in the art in the light of the foregoing disclosure, many modifications, alterations and substitutions are possible in the practice of this invention without departing from the spirit or scope thereof.

We claim:

1. A fragrance composition containing 0.1–60% by weight of one or more compounds having the structure,

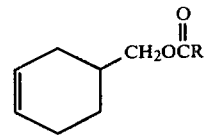

wherein R is hydrogen, a saturated or unsaturated aliphatic hydrocarbon group having from 1 to 6 carbon atoms and when unsaturated contains only one double bond, a phenyl group or a cyclopentyl group, and a fragrance carrier therefor.

2. A composition in accordance with claim 1 wherein R is propyl.

3. A composition in accordance with claim 1 wherein R is isovaleryl.

4. A composition in accordance with claim 1 wherein R is hexyl.

5. A composition in accordance with claim 1 wherein R is phenyl.

6. A composition in accordance with claim 1 wherein R is ethyl.

7. A composition in accordance with claim 1 wherein R is isobutyl.

8. A composition in accordance with claim 1 wherein R is methyl.

9. A composition in accordance with claim 1 wherein R is crotyl.

10. A composition in accordance with claim 1 wherein R is seneciyl.

11. A composition in accordance with claim 1 wherein R is cyclopentyl.

* * * * *

UNITED STATES PATENT AND TRADEMARK OFFICE
CERTIFICATE OF CORRECTION

PATENT NO. : 4,287,100
DATED : September 1, 1981
INVENTOR(S) : Kurt Kulka et al.

It is certified that error appears in the above-identified patent and that said Letters Patent are hereby corrected as shown below:

At column 3, line 45, "2400 mls. incorporated" should be --2400 mls. isopropanol--.

At column 10, line 62, "watet" should be --water--.

At column 6, line 24, "aand" should be --and--.

Signed and Sealed this

Eleventh Day of January 1983

[SEAL]

Attest:

Attesting Officer

GERALD J. MOSSINGHOFF

Commissioner of Patents and Trademarks